US006908626B2

(12) United States Patent
Cooper et al.

(10) Patent No.: US 6,908,626 B2
(45) Date of Patent: Jun. 21, 2005

(54) COMPOSITIONS HAVING A COMBINATION OF IMMEDIATE RELEASE AND CONTROLLED RELEASE CHARACTERISTICS

(75) Inventors: Eugene R. Cooper, Berwyn, PA (US); Stephen B. Ruddy, Schwenksville, PA (US)

(73) Assignee: Elan Pharma International Ltd., Shannon (IE)

( * ) Notice: Subject to any disclaimer, the term of this patent is extended or adjusted under 35 U.S.C. 154(b) by 75 days.

(21) Appl. No.: 10/268,928

(22) Filed: Oct. 11, 2002

(65) Prior Publication Data

US 2003/0137067 A1 Jul. 24, 2003

Related U.S. Application Data (60) Provisional application No. 60/328,405, filed on Oct. 12, 2001.

(51) Int. Cl.[7] ............................. A61K 9/14; A61K 9/20; A61K 9/24; A61K 9/46; A61K 9/48
(52) U.S. Cl. ..................... 424/489; 424/451; 424/452; 424/464; 424/465; 424/466; 424/472; 424/484
(58) Field of Search ....................... 424/451, 452, 424/464, 465, 466, 472, 484, 489

(56) References Cited

U.S. PATENT DOCUMENTS

| | | | |
|---|---|---|---|
| 4,178,695 A | 12/1979 | Erbeia |
| 4,616,047 A | 10/1986 | Lafon |
| 4,642,903 A | 2/1987 | Davies |
| 4,783,484 A | 11/1988 | Violante et al. |
| 4,826,689 A | 5/1989 | Violanto et al. |
| 4,997,454 A | 3/1991 | Violante et al. |
| 5,073,374 A | 12/1991 | McCarty |
| 5,110,605 A | 5/1992 | Acharya |
| 5,112,616 A | 5/1992 | McCarty |
| 5,145,684 A | 9/1992 | Liversidge et al. |
| 5,178,878 A | 1/1993 | Wehling et al. |
| 5,188,825 A | 2/1993 | Iles et al. |
| 5,215,758 A | 6/1993 | Krishnamurthy |
| 5,219,574 A | 6/1993 | Wehling et al. |
| 5,223,264 A | 6/1993 | Wehling et al. |
| 5,298,262 A | 3/1994 | Na et al. |
| 5,302,401 A | 4/1994 | Liversidge et al. |
| 5,318,767 A | 6/1994 | Liversidge et al. |
| 5,326,552 A | 7/1994 | Na et al. |
| 5,328,404 A | 7/1994 | Bacon |
| 5,336,507 A | 8/1994 | Na et al. |

(Continued)

FOREIGN PATENT DOCUMENTS

| | | | |
|---|---|---|---|
| EP | 0 352 190 A1 | 1/1990 |
| WO | WO 91/13612 A1 | 9/1991 |
| WO | WO 98/46215 A1 | 10/1998 |
| WO | WO 99/18934 A1 | 4/1999 |
| WO | WO 9918934 A1 * | 4/1999 | ............ A61K/9/14 |
| WO | WO 00/12124 A1 | 3/2000 |
| WO | WO 00/18374 A1 | 4/2000 |
| WO | WO 00/69986 A1 | 11/2000 |
| WO | WO 01/13120 A1 | 2/2001 |
| WO | WO 0145706 A1 * | 6/2001 |
| WO | WO 01/45706 A1 | 6/2001 |
| WO | WO 02/45575 A2 | 6/2002 |
| WO | WO 02/098565 A1 | 12/2002 |

Primary Examiner—Thurman K. Page
Assistant Examiner—S. Tran
(74) Attorney, Agent, or Firm—Foley & Lardner LLP (57) ABSTRACT

Disclosed are compositions exhibiting a combination of immediate release and controlled release characteristics. The compositions comprise at least one poorly soluble active ingredient having a nanoparticulate particle size, at least one surface stabilizer adsorbed onto the surface of the nanoparticulate active agent particles, and at least one active ingredient having a microparticulate particle size.

34 Claims, 3 Drawing Sheets

U.S. PATENT DOCUMENTS

| | | | |
|---|---|---|---|
| 5,340,564 | A | 8/1994 | Illig et al. |
| 5,346,702 | A | 9/1994 | Na et al. |
| 5,349,957 | A | 9/1994 | Yudelson |
| 5,352,459 | A | 10/1994 | Hollister et al. |
| 5,384,124 | A * | 1/1995 | Courteille et al. .......... 424/430 |
| 5,399,363 | A | 3/1995 | Liversidge et al. |
| 5,401,492 | A | 3/1995 | Kellar et al. |
| 5,401,513 | A | 3/1995 | Wehling et al. |
| 5,429,824 | A | 7/1995 | June |
| 5,446,464 | A | 8/1995 | Feldle |
| 5,447,710 | A | 9/1995 | Na et al. |
| 5,451,393 | A | 9/1995 | Liversidge et al. |
| 5,464,632 | A | 11/1995 | Cousin et al. |
| 5,466,440 | A | 11/1995 | Ruddy et al. |
| 5,470,583 | A | 11/1995 | Na et al. |
| 5,472,683 | A | 12/1995 | Illig |
| 5,494,683 | A | 2/1996 | Liversidge et al. |
| 5,500,204 | A | 3/1996 | Osifo |
| 5,503,846 | A | 4/1996 | Wehling et al. |
| 5,510,118 | A | 4/1996 | Bosch et al. |
| 5,518,187 | A | 5/1996 | Bruno et al. |
| 5,518,738 | A | 5/1996 | Eickhoff et al. |
| 5,521,218 | A | 5/1996 | Osifo |
| 5,525,328 | A | 6/1996 | Bacon et al. |
| 5,534,270 | A | 7/1996 | De Castro |
| 5,543,133 | A | 8/1996 | Swanson et al. |
| 5,552,160 | A | 9/1996 | Liversidge et al. |
| 5,560,931 | A | 10/1996 | Eickhoff et al. |
| 5,560,932 | A | 10/1996 | Bagchi et al. |
| 5,565,188 | A | 10/1996 | Wong et al. |
| 5,567,439 | A | 10/1996 | Myers et al. |
| 5,569,448 | A | 10/1996 | Wong et al. |
| 5,571,536 | A | 11/1996 | Eickhoff et al. |
| 5,573,749 | A | 11/1996 | Illig |
| 5,573,750 | A | 11/1996 | Singh |
| 5,573,783 | A | 11/1996 | Desieno et al. |
| 5,576,014 | A | 11/1996 | Mizumoto et al. |
| 5,580,579 | A | 12/1996 | Ruddy et al. |
| 5,585,108 | A | 12/1996 | Ruddy et al. |
| 5,587,143 | A | 12/1996 | Wong |
| 5,587,172 | A | 12/1996 | Cherukuri et al. |
| 5,587,180 | A | 12/1996 | Allen, Jr. et al. |
| 5,591,456 | A | 1/1997 | Franson et al. |
| 5,593,657 | A | 1/1997 | Ruddy et al. |
| 5,595,761 | A | 1/1997 | Allen, Jr. et al. |
| 5,607,697 | A | 3/1997 | Alkire et al. |
| 5,622,719 | A | 4/1997 | Myers et al. |
| 5,622,938 | A | 4/1997 | Wong |
| 5,628,981 | A | 5/1997 | Liversidge et al. |
| 5,631,023 | A | 5/1997 | Kearney et al. |
| 5,635,210 | A | 6/1997 | Allen, Jr. et al. |
| 5,639,475 | A | 6/1997 | Bettman et al. |
| 5,643,552 | A | 7/1997 | Illig |
| 5,662,883 | A | 9/1997 | Bagchi et al. |
| 5,665,331 | A | 9/1997 | Bagchi et al. |
| 5,709,886 | A | 1/1998 | Bettman et al. |
| 5,718,388 | A | 2/1998 | Czekai et al. |
| 5,718,919 | A | 2/1998 | Ruddy et al. |
| 5,741,522 | A | 4/1998 | Violante et al. |
| 5,747,001 | A | 5/1998 | Wiedmann et al. |
| 5,776,491 | A | 7/1998 | Allen, Jr. et al. |
| 5,776,496 | A | 7/1998 | Violante et al. |
| 5,807,576 | A | 9/1998 | Allen, Jr. et al. |
| 5,807,577 | A | 9/1998 | Ouali |
| 5,807,578 | A | 9/1998 | Acosta-Cuello et al. |
| 5,811,388 | A | 9/1998 | Friend et al. |
| 5,811,404 | A | 9/1998 | De Frees et al. |
| 5,811,422 | A | 9/1998 | Lam et al. |
| 5,811,425 | A | 9/1998 | Woods et al. |
| 5,827,541 | A | 10/1998 | Yarwood et al. |
| 5,834,025 | A | 11/1998 | de Garavilla et al. |
| 5,851,553 | A | 12/1998 | Myers et al. |
| 5,862,999 | A | 1/1999 | Czekai et al. |
| 5,866,163 | A | 2/1999 | Myers et al. |
| 5,869,098 | A | 2/1999 | Misra et al. |
| 5,871,781 | A | 2/1999 | Myers et al. |
| 6,045,829 | A | 4/2000 | Liversidge et al. |
| 6,068,858 | A | 5/2000 | Liversidge et al. |
| 6,153,225 | A | 11/2000 | Lee et al. |
| 6,165,506 | A | 12/2000 | Jain et al. |
| 6,221,400 | B1 | 4/2001 | Liversidge et al. |
| 6,264,922 | B1 | 7/2001 | Wood et al. |
| 6,267,989 | B1 | 7/2001 | Liversidge et al. |
| 6,270,806 | B1 | 8/2001 | Liversidge et al. |
| 6,316,029 | B1 | 11/2001 | Jain et al. |
| 6,375,986 | B1 * | 4/2002 | Ryde et al. .................. 424/489 |
| 6,428,814 | B1 | 8/2002 | Bosch et al. |
| 6,432,381 | B2 | 8/2002 | Liversidge et al. |
| 2002/0006919 | A1 * | 1/2002 | Thosar et al. ............... 514/175 |
| 2002/0012675 | A1 | 1/2002 | Jain et al. |
| 2003/0077329 | A1 * | 4/2003 | Kipp et al. .................. 424/489 |
| 2004/0033267 | A1 * | 2/2004 | Merisko-Liversidge et al. .......................... 424/489 |

* cited by examiner

COMPOSITIONS HAVING A COMBINATION OF IMMEDIATE RELEASE AND CONTROLLED RELEASE CHARACTERISTICS

This application claims the benefit of Provisional Application No. 60/328,405, filed Oct. 12, 2001.

FIELD OF THE INVENTION

The present invention relates to compositions exhibiting a combination of immediate release and controlled release characteristics. The compositions comprise at least one poorly soluble active ingredient having a nanoparticulate particle size, at least one surface stabilizer adsorbed onto the surface of the nanoparticulate active agent particles, and at least one poorly soluble active ingredient having a microparticulate particle size.

BACKGROUND OF THE INVENTION

A. Background Regarding Nanoparticulate Compositions

Nanoparticulate compositions, first described in U.S. Pat. No. 5,145,684 ("the '684 patent"), are particles consisting of a poorly soluble active agent having adsorbed onto the surface thereof a non-crosslinked surface stabilizer. The '684 patent also describes methods of making such nanoparticulate compositions. Nanoparticulate compositions are desirable because with a decrease in particle size, and a consequent increase in surface area, a composition is rapidly dissolved and absorbed following administration. Methods of making such compositions are described in U.S. Pat. Nos. 5,518,187 and 5,862,999, both for "Method of Grinding Pharmaceutical Substances," U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described in, for example, U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,187 for "Method of Grinding Pharmaceutical Substances;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydropropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive Nanoparticulate Compositions Having Cationic Surface Stabilizers;" and U.S. Pat. No. 6,432,381 for "Methods for Targeting Drug Delivery to the Upper and/or Lower Gastrointestinal Tract," all of which are specifically incorporated by reference. In addition, U.S. patent application Ser. No. 20020012675 A1, published on Jan. 31, 2002, for "Controlled Release Nanoparticulate Compositions," describes nanoparticulate compositions, and is specifically incorporated by reference.

Amorphous small particle compositions are described in, for example, U.S. Pat. No. 4,783,484 for "Particulate Composition and Use Thereof as Antimicrobial Agent," U.S. Pat. No. 4,826,689 for "Method for Making Uniformly Sized Particles from Water-Insoluble Organic Compounds," U.S. Pat. No. 4,997,454 for "Method for Making Uniformly-Sized Particles From Insoluble Compounds," U.S. Pat. No. 5,741,522 for "Ultrasmall, Non-aggregated Porous Particles of Uniform Size for Entrapping Gas Bubbles Within and Methods," and U.S. Pat. No. 5,776,496, for "Ultrasmall Porous Particles for Enhancing Ultrasound Back Scatter.

None of these references, or any other reference that describes nanoparticulate compositions, relates to a nanoparticulate composition having a combination of immediate release and controlled release characteristics.

B. Background Regarding Immediate Release Compositions

Conventional immediate release dosage forms, also referred to as "fast melt" or "rapidly disintegrating" dosage forms, rely on the composition of the drug matrix to effect the rapid release of the component active agent particles, rather than the particle size of the component active agent particles.

Current manufacturers of rapidly disintegrating or dissolving solid dose oral formulations include Cima Labs, Fuisz Technologies Ltd., Prographarm, R. P. Scherer, and Yamanouchi-Shaklee. All of these manufacturers market different types of rapidly dissolving solid oral dosage forms.

Cima Labs markets OraSolv®, which is an effervescent direct compression tablet having an oral dissolution time of five to thirty seconds, and DuraSolv®, which is a direct compression tablet having a taste-masked active agent and an oral dissolution time of 15 to 45 seconds. Cima's U.S. Pat. No. 5,607,697, for "Taste Masking Microparticles for Oral Dosage Forms," describes a solid dosage form consisting of coated microparticles that disintegrate in the mouth. The microparticle core has a pharmaceutical agent and one or more sweet-tasting compounds having a negative heat of solution selected from mannitol, sorbitol, a mixture of an artificial sweetener and menthol, a mixture of sugar and menthol, and methyl salicylate. The microparticle core is coated, at least partially, with a material that retards dissolution in the mouth and masks the taste of the pharmaceutical agent. The microparticles are then compressed to form a tablet. Other excipients can also be added to the tablet formulation.

WO 98/46215 for "Rapidly Dissolving Robust Dosage Form," assigned to Cima Labs, is directed to a hard, compressed, fast melt formulation having an active ingredient and a matrix of at least a non-direct compression filler and lubricant. A non-direct compression filler is typically not free-flowing, in contrast to a direct compression (DC grade) filler, and usually requires additionally processing to form free-flowing granules.

Cima also has U.S. patents and international patent applications directed to effervescent dosage forms (U.S. Pat. Nos. 5,503,846, 5,223,264, and 5,178,878) and tableting aids for rapidly dissolving dosage forms (U.S. Pat. Nos. 5,401,513 and 5,219,574), and rapidly dissolving dosage forms for water soluble drugs (WO 98/14179 for "Taste-Masked Microcapsule Composition and Methods of Manufacture").

Fuisz Technologies, now part of BioVail, markets Flash Dose®, which is a direct compression tablet containing a processed excipient called Shearform®. Shearform® is a cotton candy-like substance of mixed polysaccharides converted to amorphous fibers. U.S. patents describing this technology include U.S. Pat. No. 5,871,781 for "Apparatus for Making Rapidly Dissolving Dosage Units;" U.S. Pat. No. 5,869,098 for "Fast-Dissolving Comestible Units Formed Under High-Speed/High-Pressure Conditions;" U.S. Pat. Nos. 5,866,163, 5,851,553, and 5,622,719, all for "Process and Apparatus for Making Rapidly Dissolving Dosage Units and Product Therefrom;" U.S. Pat. No. 5,567, 439 for "Delivery of Controlled-Release Systems;" and U.S. Pat. No. 5,587,172 for "Process for Forming Quickly Dispersing Comestible Unit and Product Therefrom."

Prographarm markets Flashtab®, which is a fast melt tablet having a disintegrating agent such as carboxymethyl cellulose, a swelling agent such as a modified starch, and a taste-masked active agent. The tablets have an oral disintegration time of under one minute (U.S. Pat. No. 5,464,632).

R. P. Scherer markets Zydis®, which is a freeze-dried tablet having an oral dissolution time of 2 to 5 seconds. Lyophilized tablets are costly to manufacture and difficult to package because of the tablets sensitivity to moisture and temperature. U.S. Pat. No. 4,642,903 (R. P. Scherer Corp.) refers to a fast melt dosage formulation prepared by dispersing a gas throughout a solution or suspension to be freeze-dried. U.S. Pat. No. 5,188,825 (R. P. Scherer Corp.) refers to freeze-dried dosage forms prepared by bonding or complexing a water-soluble active agent to or with an ion exchange resin to form a substantially water insoluble complex, which is then mixed with an appropriate carrier and freeze dried. U.S. Pat. No. 5,631,023 (R. P. Scherer Corp.) refers to freeze-dried drug dosage forms made by adding xanthan gum to a suspension of gelatin and active agent. U.S. Pat. No. 5,827,541 (R. P. Scherer Corp.) discloses a process for preparing solid pharmaceutical dosage forms of hydrophobic substances. The process involves freeze-drying a dispersion containing a hydrophobic active ingredient and a surfactant in a non-aqueous phase and a carrier material in an aqueous phase.

Yamanouchi-Shaklee markets Wowtab®, which is a tablet having a combination of a low moldability and a high moldability saccharide. U.S. Patents covering this technology include U.S. Pat. No. 5,576,014 for "Intrabuccally Dissolving Compressed Moldings and Production Process Thereof," and U.S. Pat. No. 5,446,464 for "Intrabuccally Disintegrating Preparation and Production Thereof."

Other companies owning rapidly dissolving technology include Janssen Pharmaceutica. U.S. patents assigned to Janssen describe rapidly dissolving tablets having two polypeptide (or gelatin) components and a bulking agent, wherein the two components have a net charge of the same sign, and the first component is more soluble in aqueous solution than the second component. See U.S. Pat. No. 5,807,576 for "Rapidly Dissolving Tablet;" U.S. Pat. No. 5,635,210 for "Method of Making a Rapidly Dissolving Tablet;" U.S. Pat. No. 5,595,761 for "Particulate Support Matrix for Making a Rapidly Dissolving Tablet;" U.S. Pat. No. 5,587,180 for "Process for Making a Particulate Support Matrix for Making a Rapidly Dissolving Tablet;" and U.S. Pat. No. 5,776,491 for "Rapidly Dissolving Dosage Form."

Eurand America, Inc. has U.S. patents directed to a rapidly dissolving effervescent composition having a mixture of sodium bicarbonate, citric acid, and ethylcellulose (U.S. Pat. Nos. 5,639,475 and 5,709,886).

L.A.B. Pharmaceutical Research owns U.S. patents directed to effervescent-based rapidly dissolving formulations having an effervescent couple of an effervescent acid and an effervescent base (U.S. Pat. Nos. 5,807,578 and 5,807,577).

Schering Corporation has technology relating to buccal tablets having an active agent, an excipient (which can be a surfactant) or at least one of sucrose, lactose, or sorbitol, and either magnesium stearate or sodium dodecyl sulfate (U.S. Pat. Nos. 5,112,616 and 5,073,374).

Laboratoire L. LaFon owns technology directed to conventional dosage forms made by lyophilization of an oil-in-water emulsion in which at least one of the two phases contains a surfactant (U.S. Pat. No. 4,616,047). For this type of formulation, the active ingredient is maintained in a frozen suspension state and is tableted without micronization or compression, as such processes could damage the active agent.

Takeda Chemicals Inc., Ltd. owns technology directed to a method of making a fast dissolving tablet in which an active agent and a moistened, soluble carbohydrate are compression molded into a tablet, followed by drying of the tablets.

None of the described prior art teaches an immediate release dosage form in which a poorly soluble active ingredient is in a nanoparticulate form. This is significant because the prior art immediate release formulations do not address the problems associated with the bioavailability of poorly soluble drugs. While prior art immediate release dosage forms may provide rapid presentation of a drug, frequently there is an undesirable lag in the onset of therapeutic action because of the poor solubility and associated slow dissolution rate of the drug. Thus, while prior art immediate release dosage forms may exhibit rapid disintegration of the drug carrier matrix, this does not result in rapid dissolution and absorption of the poorly soluble drug contained within the dosage form.

C. Background Regarding Controlled Release Compositions

Controlled release refers to the release of an agent such as a drug from a composition or dosage form in which the agent is released according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic or diagnostic response as compared to conventional rapid release dosage forms. Such longer periods of response provide for many inherent benefits that are not achieved with the corresponding short acting, immediate release preparations. For example, in the treatment of chronic pain, controlled release formulations are often highly preferred over conventional short-acting formulations.

Controlled release pharmaceutical compositions and dosage forms are designed to improve the delivery profile of agents, such as drugs, medicaments, active agents, diagnostic agents, or any substance to be internally administered to an animal, including humans. A controlled release composition is typically used to improve the effects of administered substances by optimizing the kinetics of delivery, thereby increasing bioavailability, convenience, and patient compliance, as well as minimizing side effects associated with inappropriate immediate release rates such as a high initial release rate and, if undesired, uneven blood or tissue levels.

Prior art teachings of the preparation and use of compositions providing for controlled release of an active compound provide various methods of extending the release of a drug following administration.

Exemplary controlled release formulations known in the art include specially coated pellets, microparticles, implants, tablets, minitabs, and capsules in which a controlled release of a drug is brought about, for example, through selective breakdown of the coating of the preparation, through release through the coating, through compounding with a special matrix to affect the release of a drug, or through a combination of these techniques. Some controlled release formulations provide for pulsatile release of a single dose of an active compound at predetermined periods after administration.

U.S. Pat. No. 5,110,605 to Acharya et al. refers to a calcium polycarbophilalginate controlled release composition. U.S. Pat. No. 5,215,758 to Krishnamurthy et al. refers to a controlled release suppository composition of sodium alginate and calcium salt. U.S. Pat. No. 5,811,388 to Friend et al. refers to a solid alginate-based formulation including alginate, a water-swellable polymer, and a digestible hydrocarbon derivative for providing controlled release of orally administered compounds.

WO 91/13612 refers to the sustained release of pharmaceuticals using compositions in which the drug is complexed with an ion-exchange resin. The specific ion-exchange resin described in this published patent application is AMBER-LITE IRP 69®, a sodium polystyrene sulphonate resin.

U.S. Pat. No. 5,811,425 to Woods et al. refers to injectable depot forms of controlled release drugs made by forming microencapsule matrices of the drug in biodegradable polymers, liposomes, or microemulsions compatible with body tissues. U.S. Pat. No. 5,811,422 to Lam et al. refers to controlled release compositions obtained by coupling a class of drugs to biodegradable polymers, such as polylactic acid, polyglycolic acid, copolymers of polylactic and polyglycolic acid, polyepsilon caprolactone, polyhydroxy butyric acid, etc.

U.S. Pat. No. 5,811,404 to De Frees et al. refers to the use of liposomes having prolonged circulation half-lives to provide for the sustained release of drug compositions.

Finally, WO 00/18374, for "Controlled Release Nanoparticulate Compositions," describes controlled release formulations comprising nanoparticulate active agents.

There is a need in the art for compositions of poorly soluble drugs having a combination of immediate release and controlled release characteristics. The present invention satisfies this need.

SUMMARY OF THE INVENTION

This invention is directed to the surprising and unexpected discovery of formulations of poorly soluble active agents having a combination of immediate active agent release and controlled active agent release characteristics. The formulations comprise a combination of very small active agent particles, i.e., nanoparticulate active agent particles, in combination with larger active agent particles, i.e., micronized active agent particles, which enable obtaining the simultaneous presentation of immediate-release (IR) and controlled-release (CR) active agent components.

The nanoparticulate active agent particles, representing the IR component, afford rapid in vivo dissolution, owing to their small size and attendant large specific surface. Alternatively, micronized active agent particles, representing the CR component, afford slower in vivo dissolution, owing to a comparatively large particle size and small attendant specific surface.

IR and CR components representing a wide range of in vivo dissolution rates (and hence, in vivo input rates for absorption) can be engineered through precise control of active agent particle size. Thus, the compositions can comprise a mixture of nanoparticulate active agent particles, wherein each population of particles has a defined size correlating with a precise release rate, and the compositions can comprise a mixture of microparticulate active agent particles, wherein each population of particles has a defined size correlating with a precise release rate.

The compositions of the invention are highly unexpected, particularly since the controlled delivery of active agents has traditionally been achieved through employment of rate-controlling membranes, swellable and erodible polymers, and ion-exchange resins, rather than solely through the particle size of the active agent component of the dosage form.

In another aspect of the invention there is provided a method of preparing formulations having a combination of IR and CR characteristics. The method comprises: (1) forming a composition comprising particles of at least one nanoparticulate active agent to be administered and at least one surface stabilizer adsorbed onto the surface of the nanoparticulate active agent particles; (2), adding at least one microparticulate active agent, which can be the same or different from the active agent of (1), and (3) forming a dosage form of the mixture of (1) and (2) for administration. Additional pharmaceutically acceptable excipients can also be added to the composition for administration.

Yet another aspect of the present invention provides a method of treating a mammal, including a human, with a composition of the invention.

It is to be understood that both the foregoing general description and the following brief description of the figures and detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

A. Compositions

This invention is directed to the surprising and unexpected discovery of new compositions exhibiting a combination of IR and CR characteristics. The compositions do not require the presence of an additional ingredient, such as a rate controlling polymer or membrane, a swellable or erodible polymer, or ion-exchange resin, to obtain the CR characteristics. The IR and CR characteristics are obtained using precisely calibrated particle sizes for the one or more active agents. Smaller particle sizes result in IR profiles and larger particle sizes result in CR profiles.

The compositions of the invention comprise: (1) particles of at least one poorly soluble nanoparticulate active agent; (2) at least one surface stabilizer adsorbed onto the surface of the nanoparticulate active agent particles; and (3) at least one poorly soluble microparticulate active agent, which can be the same as or different from the active agent of (1). As taught in the '684 patent, the surface stabilizer functions to stabilize the nanoparticulate active agent by preventing agglomeration and particle size growth.

Methods of making nanoparticulate active agent compositions, which can comprise mechanical grinding, precipitation, homogenization, or any other suitable size reduction process, are known in the art and are described in, for example, the '684 patent and other prior art references disclosed in the "Background of the Invention."

The nanoparticulate and microparticulate active agent particles can be in a crystalline form, semi-crystalline form, amorphous form, semi-amorphous form, or a combination thereof.

The compositions can be formulated for administration to humans and animals via any conventional means, including but not limited to orally, rectally, parenterally (intravenous, intramuscular, or subcutaneous), intracisternally, pulmonary, intravaginally, intraperitoneally, locally (powders, ointments or drops), ocularly, aurally, or as a buccal or nasal spray.

The present invention also encompasses the compositions of the invention formulated together with one or more non-toxic physiologically acceptable carriers, adjuvants, or vehicles, collectively referred to as carriers. The compositions can be formulated for parenteral injection, oral administration in solid or liquid form, rectal or topical administration, ocular or aural administration, and the like.

For oral dosage forms, the IR component results in rapid dissolution of the poorly soluble active agent in the oral cavity as a result of the nanoparticulate size of the drug. Further, the opportunity for buccal absorption of the poorly soluble active ingredient is enhanced with the present invention. Yet another advantage of the nanoparticulate IR component is that the use of nanoparticulate active agent particles eliminates or minimizes the feeling of grittiness found with prior art IR oral formulations of poorly soluble active agents.

One advantage typically associated with IR dosage forms is a reduction of the time lag between administration of a dose and the physical presentation of the active ingredient. This lag time is usually associated with the break up of the dosage form and the distribution of the active ingredient thereafter. Another advantage of oral IR dosage forms is that the rapid presentation of the active agent in the mouth upon administration may facilitate buccal absorption of the active ingredient directly into the blood stream, thus reducing the first pass effect of the liver on the overall bioavailability of active ingredient from a unit dose. This second advantage is dramatically enhanced for the IR formulations of the invention, as the nanoparticulate size of the active agent enables rapid dissolution in the oral cavity.

It is expected that the CR component of the compositions provides effective blood levels of an incorporated active agent in a patient for an extended period of time. As used herein, "controlled release" means the release of an active agent such as a drug from a composition or dosage form in which the agent is released according to a desired profile over an extended period of time, such as from about 2 to about 24 hours or longer. Release over a longer time period is also contemplated as a "controlled release" dosage form of the present invention. An exemplary formulation is graphically illustrated below:

1. Solid Dosage Forms

In a first embodiment of the invention, both of the IR and CR components are incorporated in a solid, rapidly disintegrating or "waterless tablet" matrix intended for oral administration.

In a second embodiment of the invention, the IR and CR components are combined in a pharmaceutically acceptable tablet intended for oral administration.

In a third embodiment of the invention, the IR and CR components are combined in a pharmaceutically acceptable hard gelatin capsule intended for oral administration.

In a fourth embodiment of the invention, the IR and CR components are combined in a pharmaceutically acceptable soft gelatin capsule intended for oral administration. One variation of this dosage form comprises solubilized drug and microparticulate drug particles, in which the solubilized drug functions as the IR component and the microparticulate drug particles function as the CR component of the dosage form. This variation differs from the other dosage forms described herein in that it does not require the presence of "particulate" nanoparticulate drug particles.

In a fifth embodiment of the invention, the IR and CR components are combined in a pharmaceutically acceptable lozenge or troche intended for oral administration.

In a sixth embodiment of the invention, the IR and CR components are combined in a pharmaceutically acceptable sachet, powder, or "sprinkle" intended for oral administration.

2. Other Dosage Forms

Other suitable dosage forms include, but are not limited to, suppositories for rectal or intravaginally use; injectables, including injectables for intravenous, intramuscular, or subcutaneous administration; aerosols for pulmonary or nasal administration; buccal dosage forms; dosage forms for local application, such as powders, ointments, or drops; ocular and aural dosage forms, and dosage forms for intracisternal and intraperitoneal administration.

The IR and CR compositions of the invention can be combined in any pharmaceutically acceptable dosage form, which is not limited to those specifically described above.

3. Poorly Soluble Active Agent

The compositions of the invention comprise at least one poorly soluble therapeutic agent, diagnostic agent, or other active agent. A therapeutic agent can be a drug or pharmaceutical and a diagnostic agent is typically a contrast agent, such as an x-ray contrast agent, or any other type of diagnostic material.

The invention can be practised with a wide variety of poorly soluble drugs or diagnostic agents. The drug or diagnostic agent is preferably present in an essentially pure form, is poorly soluble, and is dispersible in at least one liquid medium. By "poorly soluble" it is meant that the drug or diagnostic agent has a solubility in a liquid dispersion medium of less than about 30 mg/ml, preferably less than about 10 mg/ml, and more preferably less than about 1 mg/ml. Such a liquid dispersion medium can be, for example, water, aqueous salt solutions, oils such as safflower oil, and solvents such as ethanol, t-butanol, hexane, and glycol.

The poorly soluble active agent can be selected from a variety of known classes of drugs or diagnostic agents, including, for example, proteins, peptides, nucleotides, anti-obesity drugs, nutraceuticals, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (e.g., hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators and xanthines.

Exemplary nutraceuticals and dietary supplements are disclosed, for example, in Roberts et al., *Nutraceuticals: The Complete Encyclopedia of Supplements, Herbs, Vitamins, and Healing Foods* (American Nutraceutical Association, 2001), which is specifically incorporated by reference. A nutraceutical or dietary supplement, also known as phytochemicals or functional foods, is generally any one of a class of dietary supplements, vitamins, minerals, herbs, or healing foods that have medical or pharmaceutical effects on the body. Exemplary nutraceuticals or dietary supplements include, but are not limited to, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, glutamine, amino acids (e.g., iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bio-engineered foods genetically engineered to have a desired property, also known as "pharmafoods."

The active agents are commercially available and/or can be prepared by techniques known in the art.

The poorly soluble active ingredient may be present in any amount which is sufficient to elicit a therapeutic effect and, where applicable, may be present either substantially in the form of one optically pure enantiomer or as a mixture, racemic or otherwise, of enantiomers.

4. Surface Stabilizers

Useful surface stabilizers, which are known in the art and described, for example, in the '684 patent, are believed to include those which physically adhere to the surface of the active agent but do not chemically bond to or interact with the active agent. The surface stabilizer is adsorbed on the surface of the nanoparticulate active agent in an amount sufficient to maintain an effective average particle size of less than about 1000 nm for the active agent. Furthermore, the individually adsorbed molecules of the surface stabilizer are essentially free of intermolecular cross-linkages. Two or more surface stabilizers can be employed in the compositions and methods of the invention.

Suitable surface stabilizers can preferably be selected from known organic and inorganic pharmaceutical excipients. Such excipients include various polymers, low molecular weight oligomers, natural products, and surfactants. Preferred surface stabilizers include nonionic and ionic surfactants, including anionic and cationic surfactants.

Representative examples of surface stabilizers include gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose phthalate, noncrystalline cellulose, magnesium aluminium silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)); Duponol P®, which is a sodium lauryl sulfate (DuPont); Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-lOG® or Surfactant 10-G® (Olin Chemicals, Stamford, Conn.); Crodestas SL-40® (Croda, Inc.); and SA9OHCO, which is $C_{18}H_{37}CH_2C(O)N(CH_3)$—$CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, random copolymers of vinyl pyrrolidone and vinyl acetate, such as Plasdone S630, PEG-derivatized phospholipids, PEG-derivatized cholesterol, PEG-derivatized cholesterol derivatives, PEG-derivatized vitamin A, PEG-derivatized vitamin E, and the like.

Other useful surface stabilizers include sodium lauryl sulfate, dioctyl sodium sulfosuccinate, or a combination thereof.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quarternary ammonium compounds, such as stearyltrimethylammonium chloride, benzyl-di(2-chloroethyl) ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyldimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, polydiallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Particularly preferred nonpolymeric primary stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$–$R_4$ are $CH_3$;
(ii) one of $R_1$–$R_4$ is $CH_3$;
(iii) three of $R_1$–$R_4$ are $CH_3$;
(iv) all of $R_1$–$R_4$ are $CH_3$;
(v) two of $R_1$–$R_4$ are $CH_3$, one of $R_1$–$R_4$ is $C_6H_5CH_2$, and one of $R_1$–$R_4$ is an alkyl chain of seven carbon atoms or less;
(vi) two of $R_1$–$R_4$ are $CH_3$, one of $R_1$–$R_4$ is $C_6H_5CH_2$, and one of $R_1$–$R_4$ is an alkyl chain of nineteen carbon atoms or more;
(vii) two of $R_1$–$R_4$ are $CH_3$ and one of $R_1$–$R_4$ is the group $C_6H_5(CH_2)_n$, where n>1;
(viii) two of $R_1$–$R_4$ are $CH_3$, one of $R_1$–$R_4$ is $C_6H_5CH_2$, and one of $R_1$–$R_4$ comprises at least one heteroatom;
(ix) two of $R_1$–$R_4$ are $CH_3$, one of $R_1$–$R_4$ is $C_6H_5CH_2$, and one of $R_1$–$R_4$ comprises at least one halogen;
(x) two of $R_1$–$R_4$ are $CH_3$, one of $R_1$–$R_4$ is $C_6H_5CH_2$, and one of $R_1$–$R_4$ comprises at least one cyclic fragment;
(xi) two of $R_1$–$R_4$ are $CH_3$ and one of $R_1$–$R_4$ is a phenyl ring; or
(xii) two of $R_1$–$R_4$ are $CH_3$ and two of $R_1$–$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference. The surface stabilizers are commercially available and/or can be prepared by techniques known in the art.

5. Particle Size

The IR characteristics of the dosage form are obtained by utilizing at least one nanoparticulate active agent having an effective average particle size of less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, or less than about 50 nm.

The CR characteristics of the dosage form are obtained by utilizing at least one microparticulate active agent having an effective average particle size of greater than about 1 micron and less than about 100 microns, less than about 90 microns, less than about 80 microns, less than about 70 microns, less than about 60 microns, less than about 50 microns, less than about 40 microns, less than about 30 microns, less than about 20 microns, less than about 10 microns, less than about 9 microns, less than about 8 microns, less than about 7 microns, less than about 6 microns, less than about 5 microns, less than about 4 microns, less than about 3 microns, or less than about 2 microns.

The compositions can comprise multiple populations of nanoparticulate active agent particles, wherein each population of particles has a defined size correlating with a precise release rate, i.e. a first population having an effective average particle size of less than about 1 micron, a second population having an effective average particle size of less than about 800 nm, a third population having an effective average particle size of less than about 500 nm, a fourth population having an effective average particle size of less than about 50 nm, etc., with each population corresponding to a specific release rate.

Similarly, the compositions can comprise multiple populations of microparticulate active agent particles, wherein each population of particles has a defined size correlating with a precise release rate, i.e. a first population having an effective average particle size of less than about 100 microns, a second population having an effective average particle size of less than about 60 microns, a third population having an effective average particle size of less than about 40 microns, a fourth population having an effective average particle size of less than about 20 microns, etc., with each population corresponding to a specific release rate.

Each population of particles in the composition, both nanoparticulate and microparticulate, exhibits a baseline resolution of at least 50%, 60%, 70%, 80%, or 90%. This means that the heterogeneous population is characterized by a multi-modal particle size distribution, with a minimum baseline resolution of 50% relative to two adjacent peaks.

50% baseline resolution is defined as half the distance from the baseline of the distribution to the average height of two adjacent peaks.

The baseline resolution of at least 50% distinguishes the claimed invention from a conventional microparticulate composition having a mixture of particle sizes, as in such a conventional composition the particle sizes are randomly distributed and do not have a baseline resolution of at least 50% for two or more particle sizes.

As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation.

By "an effective average particle size of less than about 1000 nm" it is meant that at least 50% of the active agent particles have an average particle size of less than about 1000 nm, when measured by the above techniques. Similarly, by "an effective average particle size of less than about 100 microns, it is meant that at least 50% of the active agent particles have an average particle size of less than about 100 microns, when measured by the above techniques. Preferably, at least 70% of the particles have an average particle size of less than the effective average, more preferably at least about 90% of the particles have an average particle size of less than the effective average.

6. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicifized microcrystalline cellulose (SMCC).

Suitable lubricants, including agents that act on the flowability of the powder to be compressed, are colloidal silicon dioxide, such as Aerosil® 200; talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the acid component of the effervescent couple may be present.

7. Quantities of Nanoparticulate Active Agent, Surface Stabilizer, and Microparticulate Active Agent The relative amount of at least one nanoparticulate active agent, one or more surface stabilizers, and at least one microparticulate active agent can vary widely. The optimal amount of the surface stabilizers can depend, for example, upon the particular active agent selected, the hydrophilic lipophilic balance (HLB), melting point, and water solubility of the surface stabilizer, and the surface tension of water solutions of the stabilizer, etc.

The concentration of at least one nanoparticulate active agent can vary from about 99.5% to about 0.001%, from about 95% to about 0.1%, or from about 90% to about 0.5%, by weight, based on the total combined weight of the at least one active agent and at least one surface stabilizer, not including other excipients.

The concentration of at least one surface stabilizer can vary from about 0.5% to about 99.999%, from about 5% to about 99.9%, and from about 10% to about 99.5%, by weight, based on the total combined dry weight of at least one active agent and at least one surface stabilizer, not including other excipients.

The concentration of the microparticulate active agent can vary from about 5% to about 85%, by weight, based on the total combined weight of the nanoparticulate active agent, surface stabilizer, and microparticulate active agent, not including other excipients.

B. Methods of Making Compositions of the Invention

In another aspect of the invention there is provided a method of preparing formulations having combined CR and IR characteristics. The method comprises: (1) forming a nanoparticulate composition comprising at least one nanoparticulate active agent to be administered and at least one surface stabilizer; (2) adding at least one microparticulate active agent, which is the same or different from the nanoparticulate active agent of (1), and (3) forming a suitable dosage form of the composition for administration. Pharmaceutically acceptable excipients can also be added to the composition for administration.

1. Methods of Making Nanoparticulate Compositions

Methods of making nanoparticulate compositions, which can comprise mechanical grinding, precipitation, homogenization, or any other suitable size reduction process, are known in the art and are described in, for example, the '684 patent.

Methods of making nanoparticulate compositions are also described in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" U.S. Pat. No. 5,665,331, for "Co-Microprecipitation of Nanoparticulate Pharmaceutical Agents with Crystal Growth Modifiers;" U.S. Pat. No. 5,662,883, for "Co-Microprecipitation of Nanoparticulate Pharmaceutical Agents with Crystal Growth Modifiers;" U.S. Pat. No. 5,560,932, for "Microprecipitation of Nanoparticulate Pharmaceutical Agents;" U.S. Pat. No. 5,543,133, for "Process of Preparing X-Ray Contrast Compositions Containing Nanoparticles;" U.S. Pat. No. 5,534,270, for "Method of Preparing Stable Drug Nanoparticles;" U.S. Pat. No. 5,510,118, for "Process of Preparing Therapeutic Compositions Containing Nanoparticles;" and U.S. Pat. No. 5,470,583, for "Method of Preparing Nanoparticle Compositions Containing Charged Phospholipids to Reduce Aggregation," all of which are specifically incorporated by reference.

a. Milling to Obtain Nanoparticulate Active Agent Dispersions

Milling of aqueous active agent dispersions to obtain a nanoparticulate dispersion comprises dispersing at least one active agent in a liquid dispersion medium in which the active agent is poorly soluble. By "poorly soluble" it is meant that the active agent has a solubility in a liquid dispersion medium of less than about 30 mg/ml, preferably less than about 10 mg/ml, and more preferably less than about 1 mg/ml. Such a liquid dispersion medium can be, for example, water, aqueous salt solutions, oils such as safflower oil, and solvents such as ethanol, t-butanol, hexane, and glycol.

This is followed by applying mechanical means in the presence of grinding media to reduce the particle size of the active agent to the desired effective average particle size. The active agent particles can be reduced in size in the presence of at least one surface stabilizer. Alternatively, the active agent particles may be contacted with one or more surface stabilizers after attrition. Other compounds, such as a diluent, can be added to the active agent/surface stabilizer composition during the size reduction process. Dispersions can be manufactured continuously or in a batch mode. The resultant nanoparticulate active agent dispersion can be used directly in formulating a dosage form, or the dispersion can be formulated into a powder followed by dosage formulation.

b. Precipitation to Obtain Nanoparticulate Active Agent Compositions

Another method of forming the desired nanoparticulate composition is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving the poorly water-soluble active agent in a suitable solvent; (2) adding the formulation from step (1) to a solution comprising at least one surface stabilizer to form a solution; and (3) precipitating the formulation from step (2) using an appropriate non-solvent. The method can be followed by removal of any formed salt, if present, by dialysis or diafiltration and concentration of the dispersion by conventional means. The resultant nanoparticulate active agent dispersion can be used directly in formulating a dosage form, or the dispersion can be formulated into a powder followed by dosage formulation.

c. Homogenization to Obtain Nanoparticulate Active Agent Compositions

Exemplary homogenization methods of preparing active agent nanoparticulate compositions are described in U.S. Pat. No. 5,510,118, for "Process of Preparing Therapeutic Compositions Containing Nanoparticles."

Such a method comprises dispersing active agent particles in a liquid dispersion medium, followed by subjecting the dispersion to homogenization to reduce the particle size of the active agent particles to the desired effective average particle size. The active agent particles can be reduced in size in the presence of at least one surface stabilizer. Alternatively, the active agent particles can be contacted with one or more surface stabilizers either before or after particle size reduction. It is preferred, however, to disperse the active agent particles in the liquid dispersion medium in the presence of the at least one surface stabilizer as an aid to wetting of the active agent particles. Other compounds, such as a diluent, can be added to the active agent/surface stabilizer composition either before, during, or after the size reduction process. Dispersions can be manufactured continuously or in a batch mode. The resultant nanoparticulate active agent dispersion can be used directly in formulating a dosage form, or the dispersion can be formulated into a powder followed by dosage formulation.

2. Dosage Formulation

Methods of making oral, injectable, transdermal, aerosol, buccal, topical, ocular, aural, etc. pharmaceutical formulations are known in the art, and such methods can be employed in the present invention.

In one embodiment of the invention, nanoparticulate active agent particles having at least one surface stabilizer adsorbed on to the surface of the particles can be incorporated into a dry powder matrix (e.g., through spray drying, spray granulation, or a related pharmaceutically acceptable drying process), and combined with bulk micronized active agent particles by dry blending or a similar mixing process.

In a second embodiment of the invention, nanoparticulate active agent particles can be incorporated into a dry powder matrix (e.g., through spray drying, spray granulation, or a related pharmaceutically acceptable drying process). Separately, micronized active agent particles can be incorporated into a dry powder matrix using a similar approach, and the resulting matrices can then be combined by dry blending or a similar mixing process.

In a third embodiment of the invention, micronized active agent particles can be prepared by dry milling (e.g., jet milling or pin milling).

In a fourth embodiment of the invention, micronized active agent particles can be prepared by wet milling, similar to the approach employed in the preparation of nanoparticulate active agent particles described in the '684 patent.

In an fifth embodiment of the invention, micronized active agent particles can be employed as the substrate (or a portion thereof) in a spray granulation, rotogranulation, spray coating, or related pharmaceutical process, upon which nanoparticulate active agent particles can be dispersed or deposited to form an outer layer. This particular approach facilitates the release of nanoparticulate active agent particles from the outer layer of the matrix upon exposure to biological fluids, followed by exposure and subsequent dissolution of micronized active agent particles.

In a sixth embodiment of the invention, micronized active agent particles can be employed as the substrate (or a portion thereof) in a high-shear granulation or related pharmaceutical wet-mixing process, upon which nanoparticulate active agent particles can be applied in the form of a granulating fluid. Upon drying, this particular approach enable nanoparticulate active agent particles and micronized active agent particles to be homogeneously distributed in the resulting solid matrix.

In a seventh embodiment of the invention, nanoparticulate active agent particles and micronized active agent particles can exist in the form of a dry powder or powder blend suitable for incorporation into a solid, rapidly disintegrating or "waterless tablet" matrix, the latter being attained upon compression of the dry powder or powder blend using a tablet press or similar pharmaceutically acceptable compression machine.

Exemplary spray drying, lyophilization, granulation, and tableting methods are described below.

a. Spray Drying of Nanoparticulate Dispersions

Dosage forms of nanoparticulate dispersions can be prepared by drying the nanoparticulate formulation following size reduction. A preferred drying method is spray drying. The spray drying process is used to obtain a nanoparticulate powder following the size reduction process used to transform the active agent into nanoparticulate sized particles.

In an exemplary spray drying process, the nanoparticulate active agent suspension is fed to an atomizer using a peristaltic pump and atomized into a fine spray of droplets. The spray is contacted with hot air in the drying chamber resulting in the evaporation of moisture from the droplets. The resulting spray is passed into a cyclone where the powder is separated and collected. The nanoparticulate dispersion can be spray-dried in the presence or absence of excipients to give the spray-dried intermediate powder.

The powder can be formulated, for example, into a tablet, suppository, or other solid dosage form, or the powder can be formulated into an aerosol for nasal or pulmonary administration. The powder can also be reconstituted into a liquid, and used, for example, for injectable, ocular, ear, or oral dosage forms.

b. Lyophilization

Solid dose forms of nanoparticulate dispersions can also be prepared by lyophilizing the nanoparticulate formulation following size reduction. Suitable lyophilization conditions include, for example, those described in EP 0,363,365 (McNeil-PPC Inc.), U.S. Pat. No. 4,178,695 (A. Erbeia), and U.S. Pat. No. 5,384,124 (Farmalyoc), all of which are incorporated herein by reference. Typically, the nanoparticulate dispersion is placed in a suitable vessel and frozen to a temperature of between about −5° C. to about −100° C. The frozen dispersion is then subjected to reduced pressure for a period of up to about 48 hours. The combination of parameters such as temperature, pressure, dispersion medium, and batch size will impact the time required for the lyophilization process. Under conditions of reduced temperature and pressure, the frozen solvent is removed by sublimation yielding a solid, porous, IR solid dosage form having the active ingredient distributed throughout.

The powder can be formulated, for example, into a tablet, suppository, or other solid dosage form, or the powder can be formulated into an aerosol for nasal or pulmonary administration. The powder can also be reconstituted into a liquid, and used, for example, for injectable, ocular, ear, or oral dosage forms.

c. Granulation

Alternatively, a solid oral dosage form of the invention can be prepared by granulating in a fluidized bed an admixture comprising a nanoparticulate dispersion of active agent and at least one surface stabilizer with a solution of at least one pharmaceutically acceptable water-soluble or water-dispersible excipient, to form a granulate. This is followed by tableting of the granulate to form a solid dosage form.

d. Tableting

The dosage formulations of the invention can be in the form of tablets. Preparation of such tablets can be by pharmaceutical compression or molding techniques known in the art. The tablets of the invention may take any appropriate shape, such as discoid, round, oval, oblong, cylindrical, triangular, hexagonal, and the like.

Powders for tableting can be formulated into tablets by any method known in the art. Suitable methods include, but are not limited to, milling, fluid bed granulation, dry granulation, direct compression, spheronization, spray congealing, and spray-dying. Detailed descriptions of tableting methods are provided in *Remington: The Science and Practice of Pharmacy*, 19th ed. Vol. 11 (1995) (Mack Publishing Co., Pennsylvania); and *Remington's Pharmaceutical Sciences*, Chapter 89, pp. 1633–1658 (Mach Publishing Company, 1990), both of which are specifically incorporated by reference.

The tablets may be coated or uncoated. If coated they may be sugar-coated (to cover objectionable tastes or odors and to protect against oxidation) or film coated (a thin film of water soluble matter for similar purposes).

C. Administration of the Compositions of the Invention

The present invention provides a method of treating a mammal, including a human, requiring the rapid availability of at least one poorly soluble active ingredient in combination with controlled release of the same or a different poorly soluble active ingredient. The administered compositions of the invention rapidly release an incorporated active agent resulting in fast onset of activity, and simultaneously slowly release the same or a different active agent for a prolonged pharmacological effect.

In general, the compositions of the invention will be administered to a mammalian subject in need thereof using a level of drug or active agent that is sufficient to provide the desired physiological effect. The mammalian subject may be a domestic animal or pet but preferably is a human subject. The level of drug or active agent needed to give the desired physiological result is readily determined by one of ordinary skill in the art by referring to standard texts, such as *Goodman and Gillman* and the *Physician's Desk Reference*.

The following examples are given to illustrate the present invention. It should be understood, however, that the invention is not to be limited to the specific conditions or details described in these examples. Throughout the specification, any and all references to a publicly available documents are specifically incorporated into this patent application by reference.

EXAMPLE 1

Figure 1:
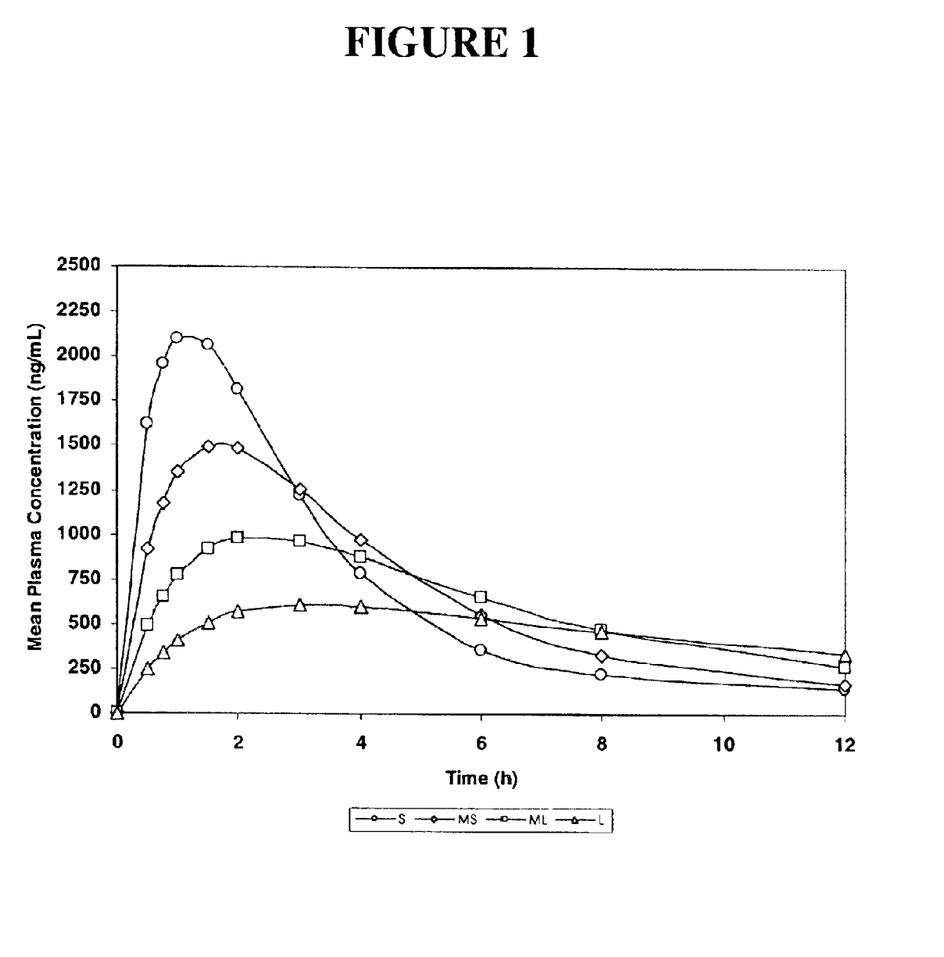
FIG. 1: Shows a simulation, using a mathematical model, of pharmacokinetic profiles following single oral doses of a pharmaceutical formulation containing an active agent having a single defined particle size.

The purpose of this example was to simulate, using a mathematical model, pharmacokinetic profiles following single oral doses of a pharmaceutical formulation containing an active agent having a single defined particle size.

The software used for the simulation was MicroMath PKAnalyst for Windows, version 1.1, MicroMath, Inc. The following assumptions were made: the active agent conforms to a 2-compartment (central and peripheral compartments) pharmacokinetic model with $1^{st}$-order absorption and $1^{st}$-order elimination from the central compartment.

D/V (dose/volume)=5000;

$K_a$>1.000 $h^{-1}$ (rate constant corresponding to the rate of dissolution);

$K_e$=0.50 $h^{-1}$ (elimination rate constant);

$K_{12}$=0.25 $h^{-1}$ (constant representing the rate of diffusion from the central compartment to the peripheral compartment); and $K_{21}$=0.125 $h^{-1}$ (constant representing the rate of diffusion from the peripheral compartment to the central compartment).

Four samples were designed, (S) small particles, (MS) medium small particles, (ML) medium large particles, and (L) particles, having the following dissolution rate constants:

dissolution rate constant for small (S) particles=1.000 h$^{-1}$
dissolution rate constant for medium small (MS) particles=0.500 h$^{-1}$
dissolution rate constant for medium large (ML) particles=0.250 h$^{-1}$
dissolution rate constant for large (L) particles=0.125 h$^{-1}$ The results of the simulation are shown in FIG. 1.

The small particle population (S) showed rapid onset of activity, peaking at a plasma concentration level of about 2100 mg/mL at a little over 1 hour following administration, with plasma levels of over 250 mg/mL several minutes following administration. However, this sample also exhibited the lowest plasma levels at 12 hours after administration.

In contrast, the large particle population (L) showed slow onset of activity, peaking at a plasma concentration level of a little over 500 mg/mL at about 2 hours after administration. However, this sample also exhibited the highest plasma levels at 12 hours after administration.

The results of the simulation demonstrate that small particles dissolve faster than larger particles, but that they also decay more rapidly. As a consequence, larger drug particles provide the longest blood plasma levels, although these same particles exhibit slow dissolution.

EXAMPLE 2

Figure 2:
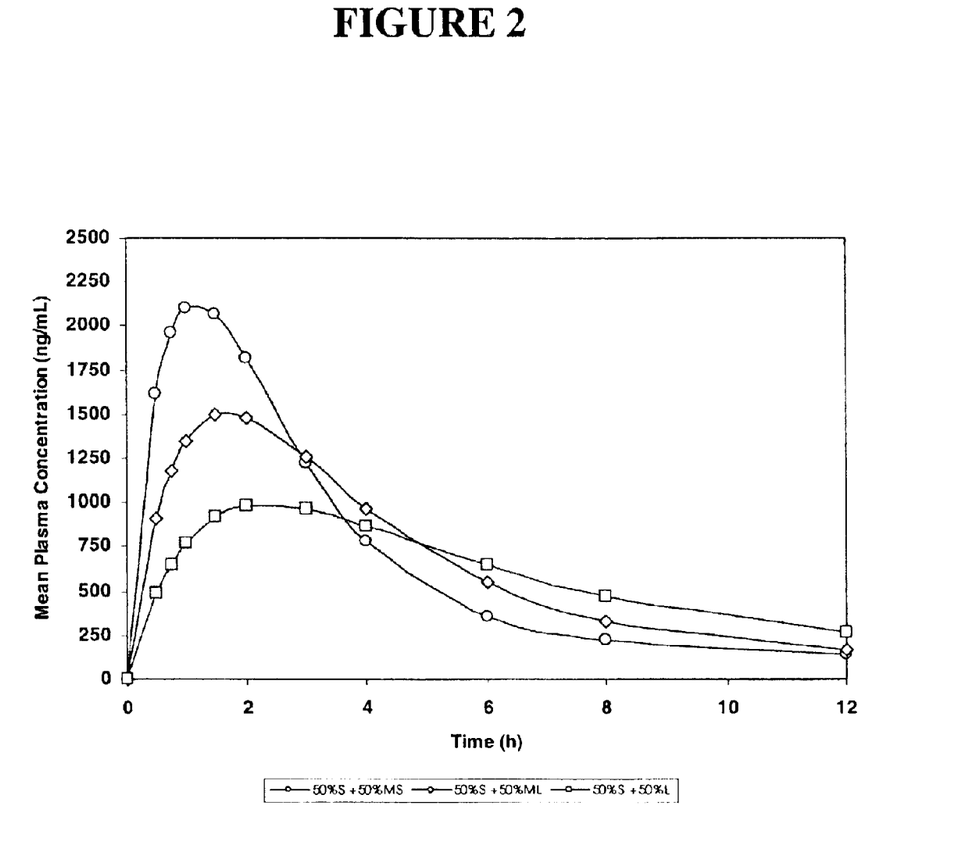
FIG. 2: Shows a simulation, using a mathematical model, of pharmacokinetic profiles following single oral doses of a pharmaceutical formulation containing mixtures of different sizes of particles.

The purpose of this example was to simulate, using a mathematical model, pharmacokinetic profiles following single oral doses of a pharmaceutical formulation containing mixtures of different sizes of particles.

The assumptions described in Example 1 are applicable to Example 2.

Simulated pharmacokinetic profiles following single oral doses of a pharmaceutical formulation containing 50:50 mixtures of small (S) particles plus medium-small (MS), medium-large (ML), or large (L) particles of an active pharmaceutical ingredient are shown in FIG. 2.

The results show, in particular, that the mixture of (S) small and (L) large particles exhibits a significantly greater maximum mean plasma concentration (almost 1000 mg/mL) as compared to the (L) large particles administered in Example 1, and the formulation also exhibits prolonged blood plasma levels, in contrast to the to the (S) small particles administered in Example 1.

EXAMPLE 3

Figure 3:
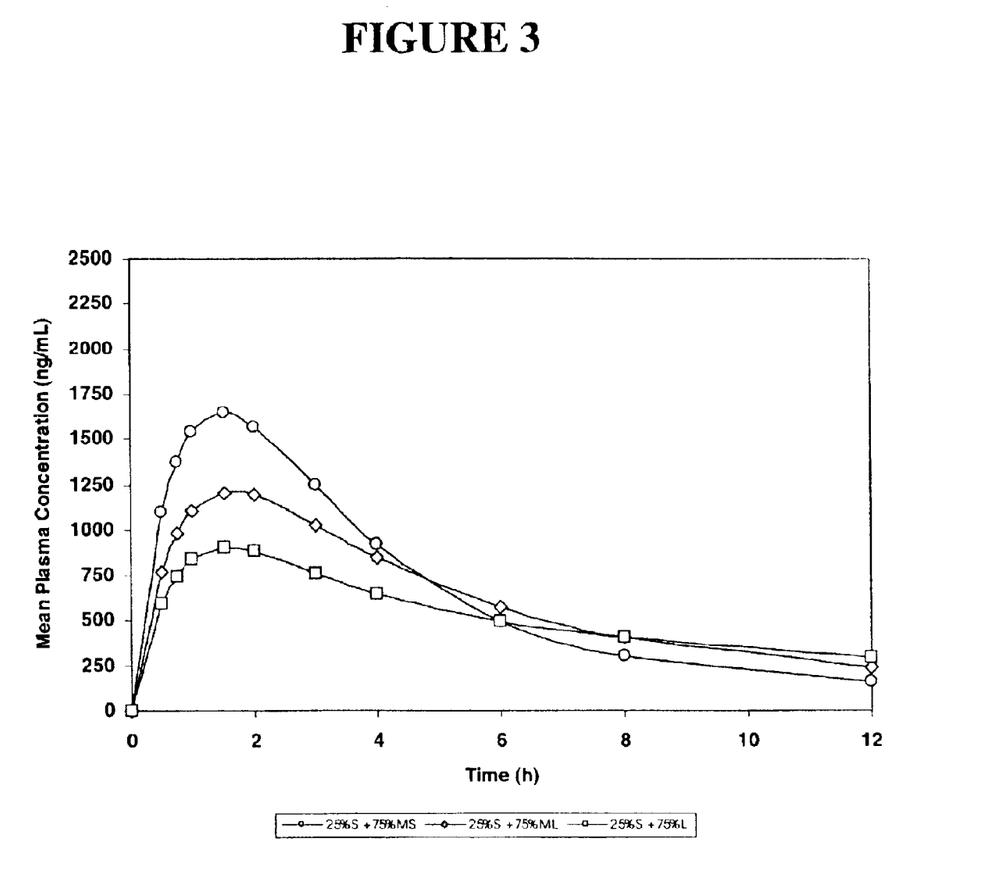
FIG. 3: Shows a simulation, using a mathematical model, of pharmacokinetic profiles following single oral doses of a pharmaceutical formulation containing mixtures of different sizes of particles.

The purpose of this example was to simulate, using a mathematical model, pharmacokinetic profiles following single oral doses of a pharmaceutical formulation containing mixtures of different sizes of particles.

The assumptions described in Example 1 are applicable to Example 3.

Simulated pharmacokinetic profiles following single oral doses of a pharmaceutical formulation containing 25:75 mixtures of small (S) plus medium-small (MS), medium-large (ML), or large (L) particles of an active pharmaceutical ingredient are shown in FIG. 3.

The results show, in particular, that the mixture of (S) small and (L) large particles exhibits a significantly greater maximum mean plasma concentration (almost 900 mg/mL) as compared to the (L) large particles administered in Example 1, and the formulation also exhibits prolonged blood plasma levels, in contrast to the to the (S) small particles administered in Example 1.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A formulation comprising:
   (a) at least one population of nanoparticulate of at least one poorly soluble active agent having an effective average particle size of less than about 1 micron;
   (b) at least one surface stabilizer adsorbed onto the surface of the nanoparticulate active agent particles wherein the concentration of the surface stabilizer is from about 0.5% to about 99.999%(w/w), based upon the total weight of the nanoparticulate active agent and the surface stabilizer, and wherein the surface stabilizer is selected from the group consisting of a nonionic surface stabilizer, an anionic surface stabilizer, a cationic surface stabilizer, and an ionic surface stabilize; and
   (c) at least one population of microparticulate active agent, which is either the same as or different from the active agent of (a), and having an effective average particle size of greater than about 1 micron and less than about 10 microns wherein the concentration of the microparticulate agent is from about 5% to about 85%, based upon the total weight of the microparticulate active agent, nanoparticulate active agent, and surface stabilizer.

2. The composition of claim 1, wherein the effective average particle size of the nanoparticulate active agent particles is selected from the group consisting of less than about 900 nm, less than about 800 nm, less than about 700 nm, less than about 600 nm, less than about 500 nm, less than about 404 nm, less than about 300 nm, less than about 250 nm, less than about 200 nm, less than about 150 nm, less than about 100 nm, and less than about 50 nm.

3. The composition of claim 1, wherein the effective average particle size of the microparticulate active agent particles is greater than about 1 micron and less than the size selected from the group consisting of less than about 9 microns, less than about 8 microns, less than about 7 microns, less than about 6 microns, less than about 5 microns, less than about 4 microns, less than about 3 microns, and less than about 2 microns.

4. The composition of claim 1 comprising more than one population of nanoparticulate active agent particles, wherein each population of particles has an effective average particle size which is less than about 1 micron.

5. The composition of claim 1 comprising more than one population of microparticulate active agent particles, wherein each population of particles has an effective average particle size which is greater than about 1 micron and less than about 10 microns.

6. The composition of claim 1, wherein the concentration of the nanoparticulate active agent is from about 99.5% to about 0.00 1%, based upon the total weight of the nanoparticulate active agent and the surface stabilizer.

7. The composition of claim 6, wherein the concentration of the nanoparticulate active agent is from about 95% to about 0.1% (w/w), based upon the total weight of the nanoparticulate active agent and the surface stabilizer.

8. The composition of claim 7, wherein the concentration of the nanoparticulate active agent is from about 90% to about 0.5% (w/w), based upon the total weight of the nanoparticulate active agent and the surface stabilizer.

9. The composition of claim 1, wherein the concentration of the surface stabilizer is from about 5% to about 99.9% (w/w), based upon the total weight of the nanoparticulate active agent and the surface stabilizer.

10. The composition of claim 9, wherein the concentration of the surface stabilizer is from about 10% to about 99.5% (w/w), based upon the total weight of the nanoparticulate active agent and the surface stabilizer.

11. The composition of claim 1 formulated into a solid, rapidly disintegrating, "waterless tablet" matrix.

12. The composition of claim 1 formulated into a pharmaceutically acceptable tablet.

13. The composition of claim 1 formulated into a pharmaceutically acceptable hard gelatin capsule.

14. The composition of claim 1 formulated into a pharmaceutically acceptable soft gelatin capsule.

15. The composition of claim 1 formulated into a pharmaceutically acceptable lozenge or troche.

16. The composition of claim 1 formulated into a pharmaceutically acceptable sachet, powder, or "sprinkle".

17. The composition of claim 1 formulated into a dosage form for oral, rectal, intravaginal, injectable, pulmonary, nasal, buccal, topical, local, intracisternal, intraperitoneal, ocular, aural, buccal spray, or nasal spray administration.

18. The composition of claim 1, wherein the formulation is made utilizing at least one method selected from the group consisting of spray drying, spray granulation, fluid bed granulation, high shear granulation, fluid bed drying, lyophilization, tableting, jet milling, pin milling, wet milling, rotogranulalion, and spray coating.

19. The composition of claim 1, wherein the nanoparticulate and microparticulate active agents are selected from the group consisting of proteins, peptides, nucleotides, anti-obesity drugs, nutraceuticals, corticosteroids, elastase inhibitors, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives, astringents, beta-adrenoceptor blocking agents, blood products and substitutes, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin and biphosphonates, prostaglandins, radio-pharmaceuticals, sex hormones, anti-allergic agents, stimulants and anoretics, sympathomimetics, thyroid agents, vasodilators, and xanthines.

20. The composition of claim 1, wherein the at least one surface stabilizer is selected from the group consisting of cetyl pyridinium chloride, gelatin, casein, phosphatides, dextran, glycerol, gum acacia, cholesterol, tragacanth, stearic acid, stearic acid esters and salts, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers, poloxamines, a charged phospholipid, dimyristoyl phophatidyl glycerol, dioctylsulfosuccinate, dialkylesters of sodium sulfosuccinic acid, sodium lauryl sulfate, alkyl aryl polyether sulfonates, mixtures of sucrose stearate and sucrose distearate, triblock copolymers of the structure: -(-PEO)—(-PBO-)—(-PEO-)-, p-isononylphenoxypoly-(glycidol), decanoyl-N-methylglucamide; n-decyl β-D-glucopyranoside, n-decyl β-D-maltopyranoside, n-dodecyl β-D-glucopyranoside, n-dodecyl β-D-maltoside, heptanoyl-N-methylglucamide, n-heptyl-β-D-glucopyranoside, n-heptyl β-D-thioglucoside, n-hexyl β-D-glucopyranoside, nonanoyl-N-methylglucamide, n-noyl β-D-glucopyranoside, octanoyl-N-methylglucamide, n-octyl-β-D-glucopyranoside, octyl β-D-thioglucopyranoside, lysozyme, a PEG derivatized phospholipid, PEG derivatized cholesterol, a PEG derivatized cholesterol derivative, PEG derivatized vitamin A, PEG derivatized vitamin E, and random copolymers of vinyl acetate and vinyl pyrrolidone.

21. The composition of claim 1, wherein the at least one cationic surface stabilizer is selected from the group consisting of a polymer, a biopolymer, a polysaccharide, a cellulosic, an alginate, a nonpolymeric compound, and a phospholipid.

22. The composition of claim 1, wherein the at least one surface stabilizer is selected from the group consisting of cationic lipids, benzalkonium chloride, sulfonium compounds, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$ dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$) dimethylbenzyl ammonium chloride, N-alkyl ($C_{14-18}$) dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-diclecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, POLYQUAT 10™, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, MIRAPOL™, ALKAQUAT™, alkyl pyridinium salts; amines, amine salts, amine oxides, imide azolinium salts, protonated quaternary acrylamides, methylated quaternary polymers, cationic guar, polymethylmethacrylate trimethylammonium bromide, polyvinylpyrrolidone-2-dimetbylaminoethyl methacrylate dimethyl sulfate, hexadecyltrimethyl ammonium bromide, poly (2-methacryloxyethyltrimethylammonium bromide) (S1001), poly(N-vinylpyrrolidone/2-dimethylaminoethyl methacrylate) di methylsulphate quarternary (S1002), and poly(2-methylacryloxyamidopropyltrimethylammonium chloride) (S1004).

23. The composition of claim 1, comprising two or more surface stabilizers.

24. The composition of claim 1, comprising sodium lauryl sulfate, dioctyl sodium sulfosuccinate, or a combination thereof, as surface stabilizers.

25. A method of preparing a formulation comprising:
(a) combining
(i) population of at least one nanoparticulate poorly soluble active agent and at least one surface stabilizer adsorbed to the surface thereof, (a) wherein the nanoparticulate active agent has an effective average particle size of less than about 1000 nm, (b) wherein the concentration of the surface stabilizer is from about 0.5% to about 99.999%(w/w), based upon the total weight of the nanoparticulate active agent and the surface stabilizer, and (c)wherein the surface stabilizer is selected from the group consisting of a nonionic surface stabilizer, an anionic surface stabilizer, a cationic surface stabilizer, and an ionic surface stabilizer and
(ii) at least one population of microparticulate active agent having an effective average particle size of greater than about 1 micron and less than about 10 microns wherein the concentration of the microparticulate agent is from about 5% to about 85%, based upon the total weight of the microparticulate active agent, nanoparticulate active agent, and surface stabilize; and
b) forming a suitable dosage formulation.

26. The method of claim 25, wherein the nanoparticulate active agent particles having at least one surface stabilizer adsorbed onto the surface of the particles are incorporated into a dry powder matrix by spray drying, spray granulation, lyophilization, or a related pharmaceutically acceptable drying process, and then combined with bulk microparticulate active agent particles by dry blending or a similar mixing process.

27. The method of claim 25, wherein:
(a) the nanoparticulate active agent particles having at least one surface stabilizer adsorbed on to the surface of the particles are incorporated into a dry powder matrix by spray drying, spray granulation, lyophilization, or a related pharmaceutically acceptable drying process;
(b) the microparticulate active agent particles are incorporated into a dry powder matrix by spray drying, spray granulation, lyophilization, or a related pharmaceutically acceptable drying process; and
(c) the resulting matrices from (a) and (b) are combined by dry blending or a similar mixing process.

28. The method of claim 25, wherein the microparticulate active agent particles are prepared by dry milling.

29. The method of claim 25, wherein the microparticulate, nanoparticulate, or both active agent particles are prepared by wet milling.

30. The method of claim 25, wherein the microparticulate active agent particles are coated with the nanoparticulate active agent/surface stabilizer particles.

31. The method of claim 30, wherein the coating is accomplished by a method selected from the group consisting of spray granulation, rotogranulation, spray coating, or a related pharmaceutical process.

32. The method of claim 25, wherein the microparticulate active agent particles are employed as a substrate in a high-shear granulation or related pharmaceutical wet-mixing process, upon which nanoparticulate active agent/surface stabilizer particles are applied in the form of a granulating fluid, wherein upon drying the nanoparticulate active agent particles and microparticulate active agent particles are homogeneously distributed in the resulting solid matrix.

33. The method of claim 25, wherein the nanoparticulate active agent/surface stabilizer particles and microparticulate active agent particles are formulated into a dry powder or powder blend for incorporation into a solid, rapidly disintegrating matrix, followed by compressing the dry powder or powder blend using a tablet press or similar pharmaceutically acceptable compression machine to form tablets.

34. A method of treating a mammal comprising administering to the mammal an effective amount of a composition according to claim 1.

* * * * *